United States Patent [19]

Smith

[11] Patent Number: 4,982,044

[45] Date of Patent: Jan. 1, 1991

[54] ALKENE COUPLING

[75] Inventor: R. Scott Smith, Baton Rouge, La.

[73] Assignee: Ethyl Corporation, Richmond, Va.

[21] Appl. No.: 374,087

[22] Filed: Jun. 30, 1989

[51] Int. Cl.$^5$ .............................................. C07C 2/24
[52] U.S. Cl. .................................................. 585/516
[58] Field of Search ........................................ 585/516

[56] References Cited

FOREIGN PATENT DOCUMENTS 868945 5/1961 United Kingdom ................ 585/516

Primary Examiner—Curtis R. Davis

Attorney, Agent, or Firm—Patricia J. Hogan; Richard J. Hammond

[57] ABSTRACT

A normal 1-alkene containing 3-8 carbons is coupled with itself, another such alkene, or ethene in the presence of a supported alkali metal as a catalyst and about 10–100 mol %, based on the amount of alkali metal catalyst, of an alkali metal hydroxide as a co-catalyst; the support being a silica having a surface area not greater than 5 m$^2$/g. In preferred embodiments of the invention, the alkene is propene or a mixture of propene and ethene, the alkali metal is potassium or a potassium alloy, and the co-catalyst is potassium hydroxide.

15 Claims, No Drawings

ALKENE COUPLING

FIELD OF INVENTION

This invention relates to the coupling of alkenes and more particularly to a method of increasing the reaction rate and product yield in such processes which are catalyzed by alkali metals.

BACKGROUND

As disclosed in U.S. Patent 3,255,272 (Lindsay), it is known that alkenes can be dimerized in the presence of alkali metal hydroxide-promoted alkali metal catalysts, which may be supported or unsupported, although the patentee appears to indicate that the supported catalysts are inferior to unsupported catalysts in the reactions. Such processes are of interest for the dimerization of alkenes in general, but they are of particular interest for the dimerization of normal 1-alkenes containing 3–8 carbons, especially propene.

The dimerization of propene typically results in the formation of a mixture of hexenes, one of which is 4-methylpentene-1, a compound which is useful as a fuel additive and as a monomer which can be employed to prepare desirable homopolymers and copolymers. The more attractive propene dimerizations are those which maximize the amount of 4-methylpentene-1 formed.

In the dimerization of alkenes, one molecule of an alkene is coupled with another molecule of the same alkene. Other alkene coupling reactions of interest are those in which one molecule of an alkene is coupled with a molecule of a different alkene, as in the coupling of propene and ethene to form pentene-1.

SUMMARY OF INVENTION

An object of this invention is to provide a novel process for coupling alkenes.

Another object is to provide such a process which utilizes a supported alkali metal as a catalyst.

A further object is to provide such a process in which the reaction rate and product yield are improved.

These and other objects are attained by heating an alkene charge comprising a normal 1-alkene containing 3–8 carbons in the presence of a supported alkali metal as a catalyst and an alkali metal hydroxide as a co-catalyst, the catalyst support being a silica which has a surface area not greater than about 5 $m^2/g$.

DETAILED DESCRIPTION

The alkene charge which is subjected to a dimerization or other coupling reaction by the process of the invention may be a single normal 1-alkene containing 3–8 carbons, i.e., propene, butene-1, pentene-1, hexene-1, heptene-1, and octene-1, or it may be a mixture of two such alkenes or a mixture of one such alkene with ethene. It is preferably propene or a mixture of propene and ethene.

As in Lindsay, the teachings of which are incorporated herein in toto by reference, the alkali metal employed as a catalyst may be lithium, sodium, potassium, rubidium, or cesium. However, it is preferably potassium or a potassium alloy, e.g., NaK. The amount used is a catalytic amount, generally about 2–10 mol%, based on the amount of alkene.

The alkali metal appropriately has its surface area increased by being finely divided or liquid as well as by being supported.

It is important that the support be a silica having a surface area not greater than about 5 $m^2/g$, e.g., about 1.3 $m^2/g$, because other conventional supports, such as alumina or a silica having a larger surface area, do not give equivalent results.

The supported catalyst is preferably prepared by dispersing the alkali metal onto the support, which may already have the co-catalyst deposited thereon, in the absence of the alkene and any diluent.

The co-catalyst of the invention is an alkali metal hydroxide, i.e., sodium, potassium, rubidium, or cesium hydroxide, and is preferably potassium hydroxide. Like the alkali metal, it is used in finely-divided form; and it may be incorporated into the reaction mixture as the hydroxide, or it may be generated in situ by reacting water with the supported alkali metal catalyst when the catalyst is sodium, potassium, rubidium, or cesium. The amount of co-catalyst employed is generally about 10–100 mol %, based on the amount of alkali metal catalyst.

The reaction is conducted by heating a mixture of the alkene, the supported catalyst, and the co-catalyst under substantially anhydrous conditions at a suitable temperature, generally about 100–250° C., preferably about 150–200° C., to dimerize the alkene or to couple two alkenes. It may be conducted in the absence of a diluent or in the presence of an excess of the alkene as the sole diluent. However, it is usually conducted in an inert diluent, e.g., a liquid alkane, cycloalkane, or aromatic hydrocarbon, such as pentane, hexane, heptane, isooctane, cyclohexane, naphthalene, decahydronaphthalane, white oils, etc.

The process of the invention proceeds at a faster rate and provides higher product yields with fewer by-products than comparable processes conducted in the absence of the co-catalyst. It is advantageous as a means of preparing compounds which are useful as solvents, internal standards, polymer intermediates, etc., and is particularly advantageous as a method of preparing 4-methylpentene-1 in a predominant amount or as a method of preparing pentene-1.

The extent to which the use of both the support and the co-catalyst increases the activity of the alkali metal catalyst is surprising. Comparison of experiments in which both the support and the co-catalyst were employed with experiments in which neither was used, experiments in which only the support was utilized, and experiments in which only the co-catalyst was utilized demonstrate that the support and co-catalyst act synergistically to provide an increase in catalytic activity that is greater than the additive effect that might have been expected from the results achieved by the use of the supports and co-catalysts separately.

The following examples are given to illustrate the invention and are not intended as a limitation thereof.

COMPARATIVE EXAMPLE A

A suitable reaction vessel was sequentially charged with 4.9 g of a diatomaceous earth silica having a surface area of 1.3 $m^2/g$, 50 g of n-heptane, 3.01 g of $C_{11}$ paraffin as an internal standard, and 1.0 g of NaK (an alloy having a K content of 78% by weight). The reactor was sealed, charged with 42 g of propene at room temperature, stirred at 750 rpm, heated to 185° C. over a period of about 17 minutes, and maintained at 185° C. for the duration of the reaction. During the reaction the stirrer was periodically stopped to allow the solids to settle; and samples were drawn, allowed to cool to room temperature, and subjected to GC analysis to determine the amounts of desired 4-methylpentene-1 (4MP1) product and 4-methylpentene-2 (4MP2), 2-methylpentene-1 (2MP1), other hexene (OHEX), and methylcyclopentane (MCP) by-products. The results of the analyses are shown below.

| Time  | Pressure | Mols × 100 | | | | |
| (hr.) | (psig) | 4MP1 | 4MP2 | 2MP1 | OHEX | MCP |
| --- | --- | --- | --- | --- | --- | --- |
| 0 | 860 | 0 | 0 | 0 | 0 | 0 |
| 1 | 840 | 0.04 | 0 | 0 | 0 | — |
| 2 | 810 | 1.70 | 0 | 0.08 | 0.08 | — |
| 3 | 770 | 3.34 | trace | 0.15 | 0.15 | — |
| 5 | 670 | 6.94 | 0.50 | 0.21 | 0.21 | 0.30 |
| 7 | 540 | 11.9 | 2.10 | 0.27 | 0.27 | 0.67 |

COMPARATIVE EXAMPLE B

Comparative Example A was essentially repeated except that the silica support was replaced with 0.48 g of −325 mesh KOH powder as a promotor. The analytical results are shown below.

| Time  | Pressure | Mols × 100 | | | | |
| (hr.) | (psig) | 4MP1 | 4MP2 | 2MP1 | OHEX | MCP |
| --- | --- | --- | --- | --- | --- | --- |
| 0 | 770 | 0 | 0 | 0 | 0 | 0 |
| 1 | 770 | 0 | 0 | 0 | 0 | — |
| 2 | 760 | trace | 0 | 0 | 0 | — |
| 4 | 720 | 0.24 | 0.13 | 0.02 | 0.01 | — |
| 6 | 660 | 1.10 | 0.40 | 0.10 | 0.10 | — |
| 7 | 620 | 2.17 | 0.67 | 0.19 | 0.17 | — |

The preceding examples demonstrate that, at least at the catalyst level employed, the use of potassium hydroxide as a promotor is ineffective in improving yield, reactivity, selectivity to 4MP1, or 4MP1/4MP2 ratio in the absence of a support. The following two examples demonstrate that these improvements are achieved when potassium hydroxide is employed in conjunction with a suitable silica support.

EXAMPLE I

Comparative Example A was essentially repeated except that the amount of NaK was increased to 1.3 g to compensate for the amount that would be subsequently reacted with water, 150 microliters of water was added to a side-arm head after the reaction temperature had been reached, and the propene was charged through the side-arm, with the side-arm head being heated with a heat gun during the first five minutes of propene charging to aid injection of the water. The analytical results are shown below.

| Time  | Pressure | Mols × 100 | | | | |
| (hr.) | (psig) | 4MP1 | 4MP2 | 2MP1 | OHEX | MCP |
| --- | --- | --- | --- | --- | --- | --- |
| 0 | 810 | 0 | 0 | 0 | 0 | 0 |
| 1 | 810 | 0 | 0 | 0 | 0 | — |
| 2 | 780 | 0.73 | trace | 0.05 | 0 | — |
| 5 | 610 | 8.70 | 0.96 | 0.70 | 0.22 | — |
| 6 | 540 | 12.40 | 1.39 | 0.96 | 0.34 | 0 |

EXAMPLE II

Comparative Example A was essentially repeated except that the 4.9 g of support was replaced with 5.5 g of a KOH-onsilica material obtained by mixing 25 g of a diatomaecous earth silica having a surface area of 1.3 m²/g with 0.82 g of KOH dissolved in 100 mL of deionized water, stripping off the water on a rotary evaporator under water aspirator produced vacuum, and subjecting the resultant powder to 165° C. under high vacuum for three hours in a rotary apparatus. The analytical results are shown below.

| Time  | Pressure | Mols × 100 | | | | |
| (hr.) | (psig) | 4MP1 | 4MP2 | 2MP1 | OHEX | MCP |
| --- | --- | --- | --- | --- | --- | --- |
| 0 | 820 | 0 | 0 | 0 | 0 | 0 |
| 1 | 810 | 0.11 | 0 | 0.01 | 0 | — |
| 2 | 760 | 2.21 | trace | 0.14 | 0 | — |
| 3 | 680 | 4.6 | 0.18 | 0.27 | 0.02 | — |
| 4 | 600 | 8.6 | 0.42 | 0.54 | 0.10 | — |
| 6 | 420 | 18.0 | 1.95 | 0.97 | 0.37 | 0 |

The following examples show that alumina and silica having a relatively high surface area are inferior to the silica supports of the invention, particularly with regard to the MP1/4MP2 ratios obtained.

EXAMPLE III

A promotor/support/catalyst composition was prepared by mixing 137 mL of 1.025 wt % aqueous KOH with 25 g of a diatomaceous earth silica having a surface area of 1.3 m²/g, stripping off the water on a rotary evaporator with water-aspiration vacuum at 55-85° C., drying the KOH/support powder at 165° C. on a rotary apparatus for three hours under high vacuum and storing it under nitrogen, and mixing 10 g of this powder with 1.2 g of NaK under nitrogen until the dispersing of NaK onto the support appeared complete.

A suitable reaction vessel was charged with the thus-prepared promotor/support/catalyst composition, 50 g of n-heptane, and 3.0 g of $C_{11}$ paraffin as an internal standard under nitrogen. The reactor was sealed, and 46 g of liquid propene was charged at room temperature. Stirring was begun, and the reactor was heated to 160° C., at which temperature the initial pressure was 720-740 psig. The analytical results are shown below.

| Time  | Mols × 100 | | | |
| (hr.) | 4MP1 | 4MP2 | 2MP1 | OHEX |
| --- | --- | --- | --- | --- |
| 2 | 0.4 | 0 | 0.01 | 0 |
| 5 | 9.5 | 0.3 | 0.5 | trace |
| 7 | 17.2 | 0.8 | 1.0 | 0.2 |

COMPARATIVE EXAMPLE C

Example III was essentially repeated except that the silica was replaced with a diatomaceous earth silica having a surface area of 20 m²/g. The analytical results are shown below.

| Time  | Mols × 100 | | | |
| (hr.) | 4MP1 | 4MP2 | 2MP1 | OHEX |
| --- | --- | --- | --- | --- |
| 2 | 0.1 | 0.2 | 0 | 0.02 |
| 4 | 0.4 | 1.2 | 0.01 | 0.1 |
| 6 | 0.3 | 2.1 | 0.09 | 0.6 |

COMPARATIVE EXAMPLE D

Example III was essentially repeated except that the silica was replaced with an alumina having a surface area of 4 m²/g. The analytical results are shown below.

| Time  | Mols × 100 | | | |
|---|---|---|---|---|
| (hr.) | 4MP1 | 4MP2 | 2MP1 | OHEX |
| 2 | 0.03 | 0.04 | 0 | 0.02 |
| 4 | 2.4 | 2.8 | 0.3 | 1.5 |
| 6 | 4.3 | 5.4 | 0.5 | 2.8 |

EXAMPLE IV

Example II was essentially repeated except that the promoter/support portion of the promotor/support-/catalyst composition was prepared by mixing 1.01 g of NaOH, 100 mL of water, and 28 g of the diatomaceous earth silica, drying the mixture to a powder, and heating the powder for three hours at 165° C. under vacuum. The analytical results are shown below.

| Time  | Mols × 100 | | | |
|---|---|---|---|---|
| (hr.) | 4MP1 | 4MP2 | 2MP1 | OHEX |
| 0 | 0 | 0 | 0 | 0 |
| 5 | 11.8 | 0.4 | 0.4 | 0.2 |
| 7 | 23.6 | 1.2 | 0.8 | 0.3 |

Comparison of the preceding example With Example III shows that sodium hydroxide appears to be superior to potassium hydroxide in acting with the support and catalyst to provide a higher conversion and selectivity to 4MP1.

COMPARATIVE EXAMPLE E

Comparative Example A was essentially repeated except that no catalyst support was employed. The analytical results are shown below.

| Time  | Pressure | Mols × 100 | | | | |
|---|---|---|---|---|---|---|
| (hr.) | (psig) | 4MP1 | 4MP2 | 2MP1 | OHEX | MCP |
| 0 | 870 | 0 | 0 | 0 | 0 | — |
| 3 | 840 | 1.3 | trace | trace | 0 | — |
| 7 | 720 | 6.7 | 1.2 | 0.5 | 0.2 | — |

Comparison of these analytical results with those given in Comparative Examples A and B and in Example II shows that the rate of 4MP1 formation can be increased by 77.6% by using the support with the catalyst, is decreased by 6.7% by using potassium hydroxide with the catalyst in the absence of the support, but is surprisingly increased by more than 168.7% when both potassium hydroxide and the support are employed together with the catalyst.

Comparison of the analytical results given in Comparative Examples A, B, and E with those given in Examples III and IV shows that in the processes conducted for seven hours the practice of the invention increases not only the rate of 4MP1 formation but the selectivity to 4MP1 and the 4MP1/4MP2 ratio (a selectivity of 67.8-78.2% in the comparative examples vs a selectivity of 89.5-91.1% in the illustrative examples; a ratio of 3.2-5.7 in the comparative examples vs a ratio of 19.7-21.5 in the illustrative examples). The higher 4MP1/4MP2 ratios constitute an important advantage because they facilitate the separation of 4MP1 from the reaction mixture by distillation. Of all the isomers 4MP2 is the one with the boiling point closest to that of 4MP1.

It is obvious that many variations may be made in the products and processes set forth above without departing from the spirit and scope of this invention.

What is claimed is:

1. In a process for coupling a normal 1-alkene containing 3-8 carbons with itself, another such 1-alkene, or ethene in the presence of a supported alkali metal as a catalyst and an alkali metal hydroxide as a co-catalyst, the improvement which comprises employing as the catalyst support a silica having a surface area not greater than about 5 $m^2/g$.

2. The process of claim 1 wherein the alkene is propene, which is coupled with itself.

3. The process of claim wherein the alkene is propene, which is coupled with ethene.

4. The process of claim 1 wherein the alkali metal catalyst is potassium or a potassium alloy.

5. The process of claim 4 wherein the alkali metal catalyst is potassium.

6. The process of claim 4 wherein the alkali metal catalyst is NaK.

7. The process of claim 1 wherein the catalyst support is a diatomaceous earth silica having a surface area of about 1.3 $m^2g$.

8. The process of claim 1 wherein the co-catalyst is potassium hydroxide.

9. The process of claim 1 wherein the supported alkali metal catalyst is prepared by dispersing the alkali metal onto the support in the absence of the alkene and any diluent.

10. The process of claim 1 which is conducted at a temperature of about 100-250° C.

11. The process of claim 10 wherein the temperature is about 150-200° C.

12. A process for preparing 4-methylpentene-1- which comprises heating propene at 150-200° C. in the presence of a supported NaK catalyst and about 10-100 mol %, based on the amount of NaK, of potassium hydroxide co-catalyst; the support being a diatomaceous earth silica having a surface area of about 1.3 $m^2/g$.

13. A process for preparing 4-methylpentene-1 which comprises heating propene at 150-200° C. in the presence of a supported NaK catalyst and about 10-100 mol %, based on the amount of NaK, of sodium hydroxide co-catalyst; the support being a diatomaceous earth silica having a surface area of about 1.3 $m^2/g$.

14. The process of claim 1 wherein pentene-1 is prepared by heating a mixture of propene and ethene at 150-200° C. in the presence of a supported NaK catalyst and about 10-100 mol %, based on the amount of NaK, of potassium hydroxide co-catalyst; the support being a diatomaceous earth silica having a surface area of about 1.3 $m^2/g$.

15. The process of claim 1 wherein pentene-1 is prepared by heating a mixture of propene and ethene at 150-200° C. in the presence of a supported NaK catalyst and about 10-100 mol %, based on the amount of NaK, of sodium hydroxide co-catalyst; the support being a diatomaceous earth silica having a surface area of about 1.3 $m^2/g$.

* * * * *

UNITED STATES PATENT AND TRADEMARK OFFICE
CERTIFICATE OF CORRECTION

PATENT NO. : 4,982,044

DATED : January 1, 1991

INVENTOR(S) : R. Scott Smith

It is certified that error appears in the above-identified patent and that said Letters Patent is hereby corrected as shown below:

On the title page, the Serial Number reads "374,087" and should read --374,057--.

Column 6, line 16, reads "claim wherein" and should read --claim 1 wherein--.

Signed and Sealed this

Fourteenth Day of July, 1992

Attest:

DOUGLAS B. COMER

*Attesting Officer*   Acting Commissioner of Patents and Trademarks